US011964129B2

(12) United States Patent
Shih et al.

(10) Patent No.: US 11,964,129 B2
(45) Date of Patent: Apr. 23, 2024

(54) IMPLANTABLE CONTINUOUS-FLOW PUMPS

(71) Applicant: MiniPumps LLC, Pasadena, CA (US)

(72) Inventors: Jason Shih, Yorba Linda, CA (US); Gregory Harbers, Montrose, CA (US); Richard Purvis, Pasadena, CA (US); Miho Matsuoka, Rosemead, CA (US); Andrew Urazaki, Las Vegas, NV (US); Mark Humayun, Glendale, CA (US); William Andrew Brandt, Castaic, CA (US); Atoosa Lotfi, Valencia, CA (US); Didier Sagan, San Diego, CA (US); Andrew Dunn, Santa Monica, CA (US)

(73) Assignee: MiniPumps LLC, Pasadena, CA (US)

( * ) Notice: Subject to any disclaimer, the term of this patent is extended or adjusted under 35 U.S.C. 154(b) by 424 days.

(21) Appl. No.: 16/290,501

(22) Filed: Mar. 1, 2019

(65) Prior Publication Data

US 2019/0269850 A1 Sep. 5, 2019

Related U.S. Application Data

(60) Provisional application No. 62/637,007, filed on Mar. 1, 2018.

(51) Int. Cl.
*A61M 5/142* (2006.01)
*A61F 9/00* (2006.01)
(Continued)

(52) U.S. Cl.
CPC ....... *A61M 5/14276* (2013.01); *A61F 9/0017* (2013.01); *A61F 9/0026* (2013.01);
(Continued)

(58) Field of Classification Search
CPC .............. A61M 5/141; A61M 5/14204; A61M 5/14276; A61M 5/14513; A61M 5/14586; A61M 5/14593; A61M 5/148; A61M 5/1483; A61M 5/1486; A61M 5/155; A61M 5/16881; A61M 5/172; A61M 5/482; A61M 5/484; A61M 2005/14284; A61M 2005/3114; A61M 2005/3128; A61M 39/0208; A61M 2039/0223–0232; A61M 2039/0235; A61M 2039/0238; A61M 2039/0241; A61M 2039/0244; A61M 2039/242; A61M 2205/04; A61M 2205/3334; A61M 2205/75;
(Continued)

(56) References Cited

U.S. PATENT DOCUMENTS 4,241,757 A 12/1980 Bron
4,714,462 A 12/1987 DiDomenico
(Continued)

*Primary Examiner* — Kami A Bosworth
(74) *Attorney, Agent, or Firm* — Morgan, Lewis & Bockius LLP

(57) ABSTRACT

In various embodiments, a drug pump includes a housing and, within the housing, an expandable drug reservoir at least part of which is exposed to a pressurized propellant. The propellant exerts a substantially constant pressure on the drug reservoir. A flow restrictor significantly limits outflow from the pump, and preferably has both a small diameter and a long path length, which acts to control the outflow from the drug reservoir. As a result, the pump produces a substantially constant outflow.

23 Claims, 14 Drawing Sheets

(51) Int. Cl.
*A61M 5/14* (2006.01)
*A61M 5/148* (2006.01)
*A61M 5/155* (2006.01)
*A61M 5/168* (2006.01)
*A61M 5/172* (2006.01)
*A61M 5/145* (2006.01)
*A61M 39/02* (2006.01)
*A61M 39/24* (2006.01)

(52) U.S. Cl.
CPC .......... *A61M 5/141* (2013.01); *A61M 5/1483* (2013.01); *A61M 5/1486* (2013.01); *A61M 5/155* (2013.01); *A61M 5/16881* (2013.01); *A61M 5/172* (2013.01); *A61M 5/14593* (2013.01); *A61M 39/0208* (2013.01); *A61M 2039/242* (2013.01); *A61M 2205/04* (2013.01); *A61M 2205/75* (2013.01); *A61M 2205/7518* (2013.01); *A61M 2205/7527* (2013.01); *A61M 2205/7545* (2013.01); *A61M 2210/0612* (2013.01)

(58) Field of Classification Search
CPC .. A61M 2205/7518; A61M 2205/7527; A61M 2205/7545; A61M 2205/8218–8231; A61M 2210/0612; A61M 2005/14204; A61M 2005/14513; A61F 9/0017; A61F 9/0026
See application file for complete search history.

(56) References Cited

U.S. PATENT DOCUMENTS

| | | | | |
|---|---|---|---|---|
| 4,969,873 A | * | 11/1990 | Steinbach | A61M 5/14276 128/DIG. 12 |
| 4,978,338 A | * | 12/1990 | Melsky | A61M 5/14276 604/132 |
| 5,176,644 A | * | 1/1993 | Srisathapat | A61M 5/14276 128/DIG. 12 |
| 5,957,890 A | * | 9/1999 | Mann | A61M 5/14276 604/131 |
| 5,978,338 A | * | 11/1999 | Nakamura | G11B 27/3027 369/59.19 |
| 6,280,416 B1 | * | 8/2001 | Van Antwerp | A61M 5/14276 128/DIG. 12 |
| 7,931,643 B2 | | 4/2011 | Olsen et al. | |
| 8,529,538 B2 | | 9/2013 | Pang et al. | |
| 2003/0050623 A1 | * | 3/2003 | Lord | A61M 5/14224 604/891.1 |
| 2006/0089619 A1 | * | 4/2006 | Ginggen | A61M 5/14276 604/891.1 |
| 2006/0259016 A1 | * | 11/2006 | Steinbach | A61M 5/14276 604/891.1 |
| 2006/0271021 A1 | * | 11/2006 | Steinbach | A61M 5/14276 604/891.1 |
| 2007/0016171 A1 | * | 1/2007 | Podvin | A61M 5/16877 604/891.1 |
| 2007/0043335 A1 | * | 2/2007 | Olsen | A61M 5/14276 604/890.1 |
| 2011/0106010 A1 | * | 5/2011 | Steinbach | A61M 5/14593 141/3 |
| 2012/0253270 A1 | * | 10/2012 | Steinbach | A61K 9/0024 604/67 |
| 2013/0184640 A1 | * | 7/2013 | Li | A61M 5/14526 604/67 |
| 2016/0206811 A1 | | 7/2016 | Shih et al. | |
| 2016/0278899 A1 | * | 9/2016 | Heller | A61K 9/0053 |
| 2017/0116025 A1 | | 4/2017 | Ghosh et al. | |

* cited by examiner

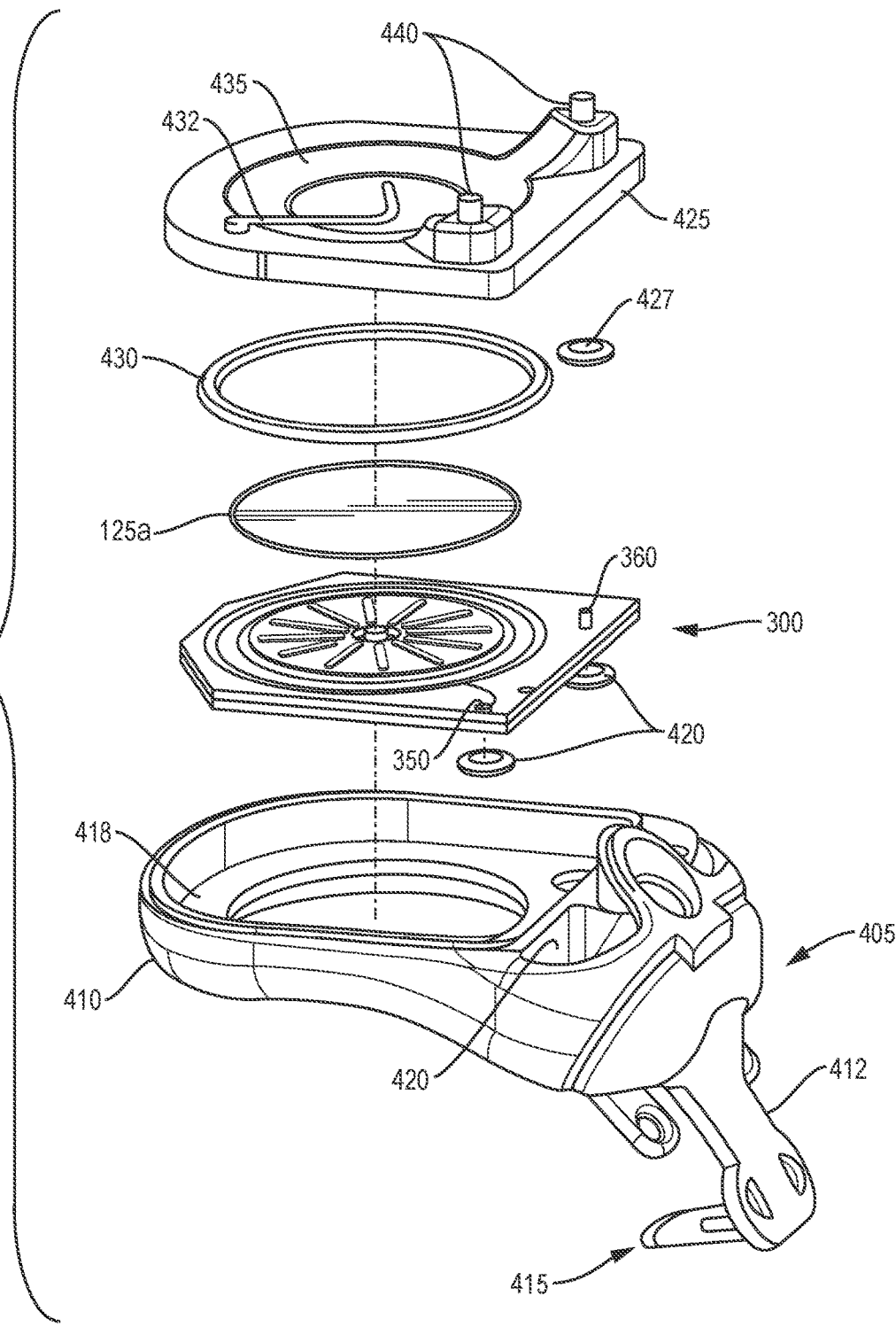

IMPLANTABLE CONTINUOUS-FLOW PUMPS

RELATED APPLICATION

This application claims the benefit of and priority to U.S. Provisional Patent Application No. 62/637,007, filed Mar. 1, 2018, the entire disclosure of which is hereby incorporated herein by reference.

TECHNICAL FIELD

In various embodiments, the present invention relates generally to implantable pumps for, e.g., drug administration.

BACKGROUND

Medical treatment often requires the administration of a therapeutic agent (e.g., medicament, drugs, etc.) to a particular part of a patient's body. As patients live longer and are diagnosed with chronic and/or debilitating ailments, the need to place even more protein therapeutics, small-molecule drugs, and other medications into targeted anatomical areas will only increase. Some maladies, however, are difficult to treat with currently available therapies and/or require administration of drugs to difficult-to-reach anatomical regions. Many of these therapies would benefit from concentrated target-area treatment, which would reduce systemic side effects. Furthermore, certain drugs such as protein therapeutics are expensive, costing thousands of dollars per vial. For these reasons, new and improved approaches to targeted drug delivery are constantly sought.

Implantable drug-delivery devices with refillable drug reservoirs address and overcome many of the problems associated with conventional drug-delivery modalities. They generally facilitate controlled delivery of pharmaceutical solutions to a specified target. As the contents of the drug reservoir deplete, a clinician may refill the reservoir in situ, i.e., while leaving the device implanted within the patient's body.

As implantable devices of varying sizes, dosing capabilities, and implant locations become available, the reliable delivery of drugs over long periods of time (e.g., bi-weekly or monthly, or continuous dosing over two or more years) becomes progressively more complicated. At the same time, clinical acceptance increasingly requires delivery systems with minimal intervention requirements (i.e., drug refilling, modification, and replacement) to reduce patient discomfort and increase patient compliance and quality of life.

Therefore, new drug-delivery configurations capable of addressing these escalating and difficult-to-reconcile requirements are constantly being sought.

SUMMARY

In various embodiments, the invention relates to a drug pump including a housing and, within the housing, an expandable drug reservoir at least part of which is exposed to a pressurized propellant. The propellant exerts a substantially constant pressure on the drug reservoir. A flow restrictor significantly limits outflow from the pump, and preferably has both a small diameter and a long path length, which acts to control the outflow from the drug reservoir. As a result, the pump produces a substantially constant outflow, and embodiments of the invention contain no circuitry and/or no valving—just a continuous flow path from drug chamber to cannula.

Accordingly, in a first aspect, the invention pertains to an implantable pump comprising, in various embodiments, a rigid housing; within the housing, a drug reservoir having an expandable membrane affixed to an equatorial rib having a rounded ridge profile to limit material stress on the membrane when in contact therewith; a propellant chamber occupying interior space of the housing, where a propellant within the chamber exerts a substantially constant pressure on the drug reservoir; a cannula in fluid communication with the drug reservoir; and a flow restrictor between the drug reservoir and the cannula.

In some embodiments, the drug reservoir has a pair of expandable membranes affixed to first and second opposed sides of the equatorial rib; and the first and second sides of the equatorial rib have rounded ridge profiles to limit material stress on the membranes when in contact therewith. In other embodiments, the drug reservoir has a single membrane encapsulating the equatorial rib and the equatorial rib has first and second opposed sides with rounded ridge profiles to limit material stress on the membrane when in contact therewith.

The pump may further include a refill port fluidically coupled to the drug reservoir and having a self-sealing entry port in the rigid housing. The flow restrictor may be sized to permit an outflow from the cannula ranging from 0.1 µL/day to 20 µL/day. For example, the flow restrictor, which may be a microfluidic chip, may have a fluid path with a cross-sectional area ranging from 50 $\mu m^2$ to 400 $\mu m^2$.

In some embodiments, the pump further comprises a filter and an ante-chamber intervening between the drug reservoir and fluid lines leading to the cannula. The pump may also include a refill port in the housing for filling the drug chamber, with the ante-chamber facilitating flushing of the bacterial filter through one of the fluid lines.

In various embodiments, the propellant has a pressure sufficient to eject all liquid contents of the drug reservoir. The propellant may be a material mixture that generates a total pressure greater than the pressure at the target site at body temperature.

The equatorial rib may have one or a plurality of bores therethrough. For example, the equatorial rib may have at least two diametrically opposed bores therethrough. One of the bores may extend in a direction perpendicular to the direction of compression of the drug reservoir by the propellant.

In some embodiments, the pump may include an ante-chamber between the drug reservoir and the flow restrictor. The pump may include at least one filter in line between the drug reservoir and the flow restrictor. The pump may have a propellant fill port including a self-sealing elastomeric septum. The propellant, for its part, may have as a pressure adjustable by heating.

In some embodiments, the pump includes a pressure-threshold bypass fluidic path for conveying to the cannula fluid injected through the refill port. The bypass fluidic path may include a pressure-triggered check valve.

Particularly for ocular applications, the pump may include at least one drainage cannula.

In another aspect, the invention pertains to an implantable pump comprising, in various embodiments, a rigid housing; within the housing, a compressible drug reservoir; a propellant chamber occupying interior space of the housing, a propellant therein exerting a substantially constant pressure on the drug reservoir; a cannula in fluid communication with the drug reservoir; a flow restrictor between the drug reservoir and the cannula; and an ante-chamber between the drug reservoir and the flow restrictor.

The pump may further comprise a filter and a refill port in the housing for filling the drug chamber, where the ante-chamber facilitates flushing of the bacterial filter via the refill port.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately" and "substantially" mean±10%, and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4A is an exploded view of a lower housing member and various components of a drug pump in accordance with embodiments of the invention.

DETAILED DESCRIPTION

The present invention relates to, generally, drug delivery devices, e.g., ocular drug pumps, implantable insulin pumps, inner ear pumps, and brain pumps. Embodiments of the invention address limitations affecting many slow-response pump actuation mechanisms (e.g., electro-osmosis and electrolysis), in particular the fact that for temporally separated doses, each successive dose requires more time and/or power to complete. Also, without accurate flow sensors and related programming, slow-response actuation mechanisms have difficulty replicating dose and/or long-term delivery volumes with microliter or picoliter accuracy. Embodiments described below provide efficient actuation as well as increased reliability of reservoirs, fluid paths, and components. In general, the drug reservoir is connected to the outside of a shell by an accessible refill port and also to a cannula leading to the target site.

The embodiments described below involve actuation mechanisms that are presented as non-limiting examples; working implementations may vary in terms of the shape and movement profile of the actuation member (e.g., a circularly corrugated diaphragm deflecting into a dome, a piston or bellows deflecting in only one dimension, etc.), and different types of force-transmitting actuators may be used interchangeably herein. In some embodiments, specific structures enhancing or assisting actuation are described. The most suitable type and configuration of actuation member will depend on the application and may be readily identified by those skilled in the art without undue experimentation. Often the primary goal is to minimize the overall size/volume of the drug delivery device. Furthermore, actuating diaphragms are preferentially thinner in specific regions to allow for preferential deflection and low-power actuation. By adapting an actuation profile to the specific curvatures of a device (which may themselves be dictated by the anatomy of an implant site), reliability and operational lifetime may be increased.

Figure 1A:
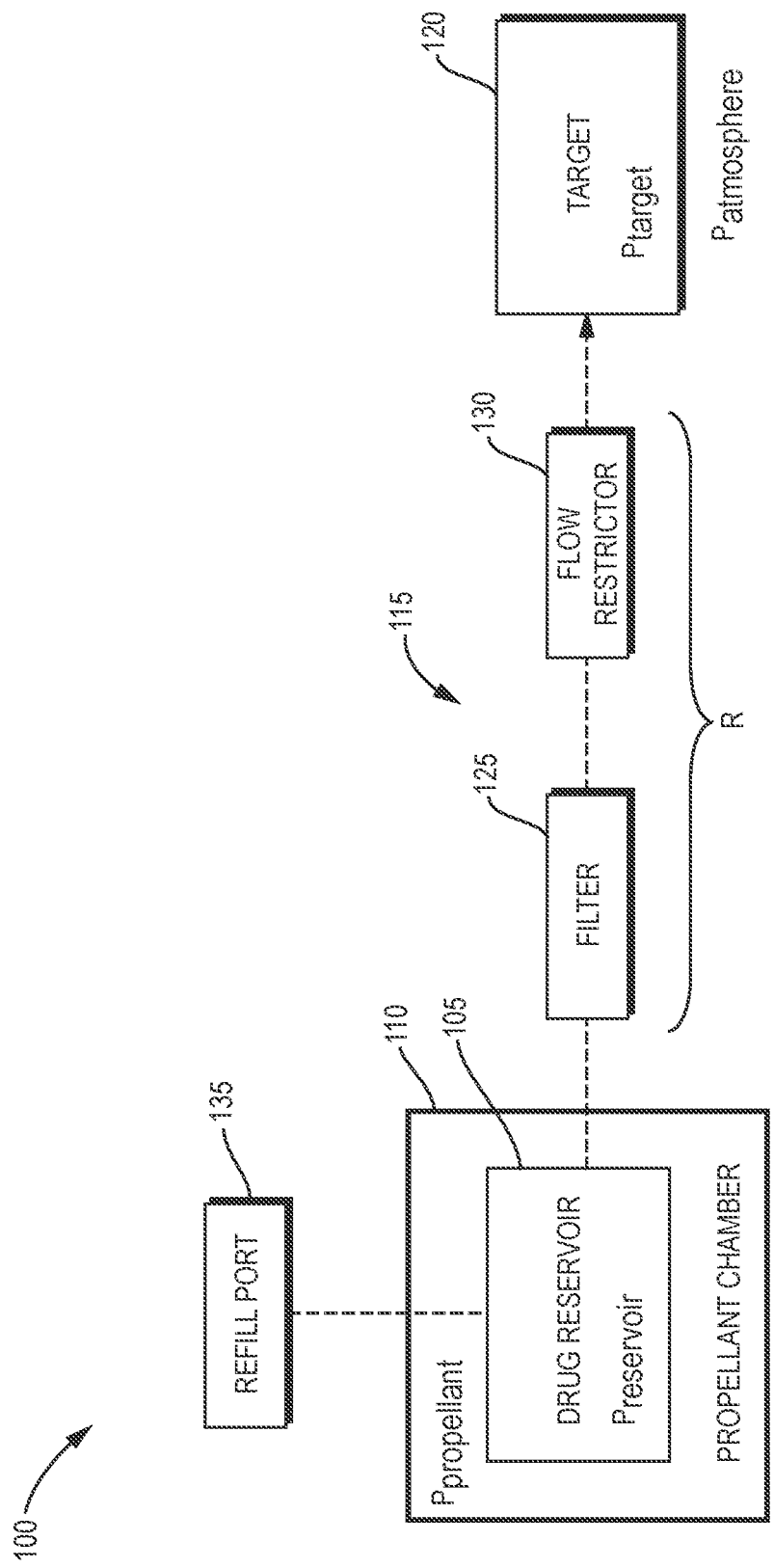
FIGS. 1A and 1B schematically illustrate components of a representative embodiment.
Figure 1B:
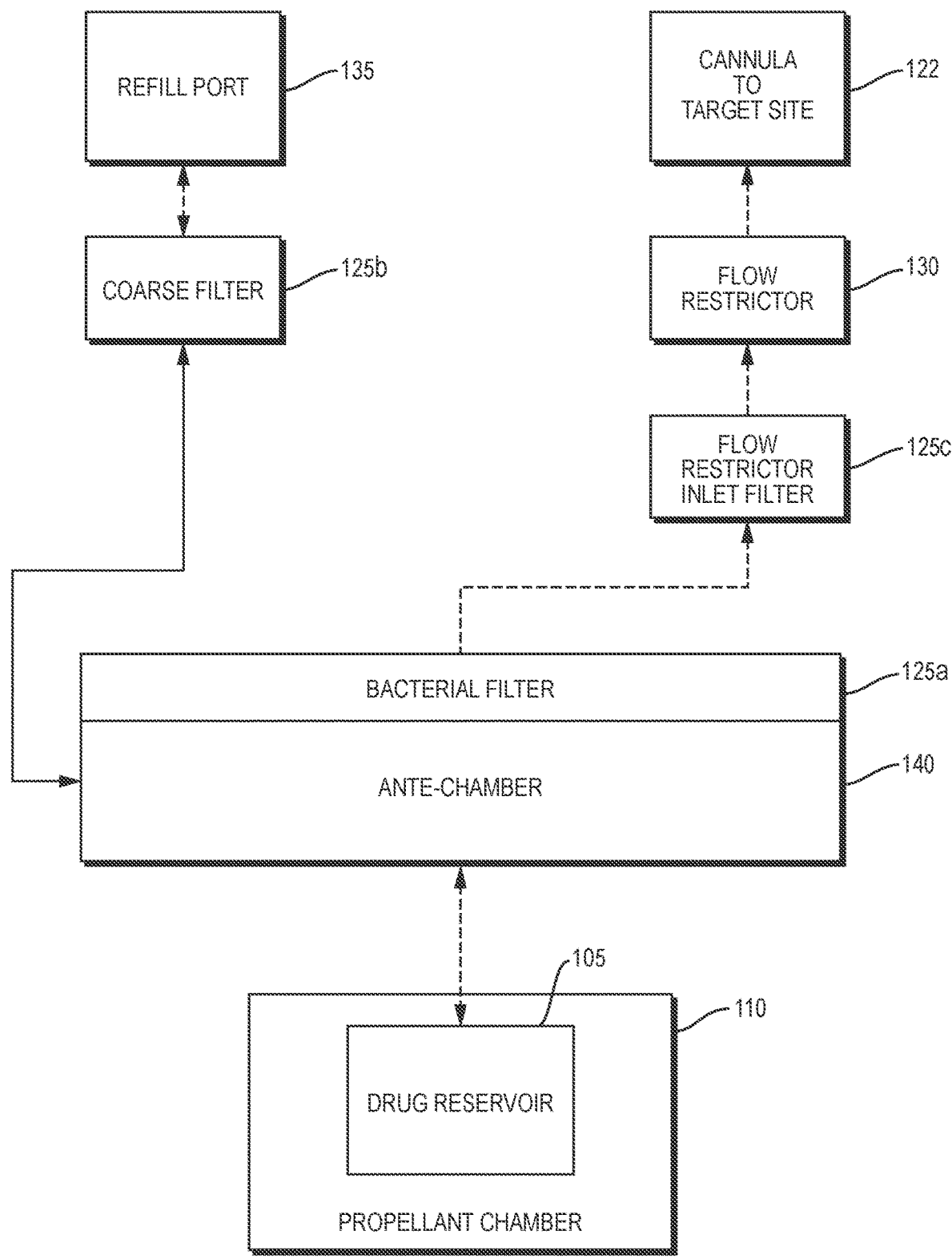

FIGS. 1A and 1B schematically depict the basic features, their interaction, and the mode of operation of various embodiments hereof. As illustrated, a pump device 100 includes a collapsible drug reservoir 105 fluidically surrounded, in whole or in part, by a propellant chamber 110. Introduction of propellant into the chamber 110 or, more typically, expansion of propellant therewithin exerts isotropic pressure on at least a portion of the drug reservoir, forcing liquid contained therein through an exit fluid path 115 to an external target region 120, generally via a cannula 122. The fluid path 115 includes a filter 125 and a flow restrictor 130. A refill port 135 facilitates replenishment of the drug reservoir 105.

The flow restrictor 130 is configured to achieve a target delivery rate given the overall pressure drop $P_{reservoir}-P_{target}$, since for laminar flow, the mass transfer rate Q, the pressure drop ΔP, and the flow resistance R are related as $$R = \frac{Q}{\Delta P}.$$

It is also found that flow stability is improved by maintaining a constant pressure difference between the propellant chamber 110 and the drug reservoir 105 (i.e., $P_{propellant}-P_{reservoir}$) as well as a relatively high absolute propellant pressure. The constant pressure difference can be maintained by filling the propellant chamber 110 with propellant amply, i.e., beyond the threshold required to maintain a constant pressure at the drug reservoir's minimum volume. A high propellant pressure maintains a large difference between the reservoir pressure and the pressure at the target delivery site, including the possible changes in atmospheric pressure or changes in pressure drop across the drug reservoir, so that these do not materially affect flow. A mixture of propellants may be selected that are minimally temperature sensitive (i.e., each unit change in temperature results in a small change in vapor pressure). If these measures are taken, the reservoir pressure will remain fairly constant in the normal range of temperature even as the drug reservoir empties, and the pressure can be pre-set during manufacture. Coupled with the flow restrictor 130, this feature enables the device to maintain a stable drug delivery rate throughout its life.

As further shown in FIG. 1B, the system may contain more than a single filter 125. A bacterial or other filter 125a (e.g., a 0.2 μm filter or otherwise sized to exclude particular organisms) may intervene between the drug reservoir 105 and the fluid path 115; a coarse filter 125b for preventing the entry of large particles may additionally intervene between the refill port 135 and the ante chamber 140; and an flow restrictor inlet filter 125c may additionally intervene between the drug reservoir 105 and the fluid path 115. The bacterial filter 125a is typically made of a hydrophilic material, and may therefore filter bubbles as well. The flow restrictor inlet filter 125c, if present, prevents any protein aggregate formed through denaturing, tertiary folding patterns, and clumping from adversely affecting the flow rate through the downstream flow restrictor 130. Further filters may also be added, including a second bacterial filter (not shown) after the refill port to prevent bacteria from entering into the drug reservoir.

A small "ante-chamber" 140 may be disposed between the drug reservoir 105 and both the refill port 135 and the fluid path 115. The ante-chamber 140 facilitates flushing of the bacterial filter 125a to remove any biologic aggregate or other debris. The ante-chamber 140 may further contain internal features (e.g., grooves, side ports, etc.) to trap drug aggregate or air bubbles and prevent their exit through the cannula 122. Drug aggregates are ideally retained in grooves, wells, or side ports within the ante-chamber 140, and are flushed out during the refill process. Air bubbles, if traveling through the flow restrictor, could variably compress and expand, thereby affecting the overall flow until expelled.

During the refill process, the liquid drug enters the refill port 135, travels through the coarse filter 125b (if present), and to the drug reservoir via the ante-chamber 140. As the applied pressure of the refill system is greater than the constant pressure exerted on the drug reservoir 105 by the propellant in the propellant chamber 110, the drug reservoir 105 will expand and fill with drug. During use of the pump device 100, the drug will flow from the drug reservoir 105 through the ante-chamber 140, the bacterial and flow restrictor inlet filters 125a, 125b (if present), the flow restrictor 130, and finally to the target site via the cannula 122.

In one embodiment, the propellant is a material mixture that generates a total pressure greater than the target site pressure at body temperature. In many embodiments, the propellant is a mixture of gas and liquid and may contain a material capable of changing phase from liquid to gas within the range of body temperature. For example, the propellant may be perfluoropentane. In other embodiments, the propellant may comprise or consist of two or more components that are non-miscible, in which case the vapor pressures of the two components are additive. In yet another embodiment, the propellant comprises two or more components that are miscible, in which case the total pressure is the weighted average, by mole fraction, of the vapor pressures of each component (as described for an ideal mixture in Raoult's law). With this approach, the propellant is not released or created for actuation purposes; rather, it is "always on," and control over drug dispensing is accomplished by flow control instead of pump actuation. The propellant chamber 110 may also contain a "getter" or other gas-absorption material, such as magnesium or calcium, to absorb unwanted gases in the propellant chamber and prevent their partial pressures from changing the overall propellant pressure. An advantage to this approach is that the profile of the drug reservoir need not match the deflection profile of an expandable diaphragm, as in many electrolysis-actuated pumps, resulting in greater design flexibility and the potential for decreasing overall device size. The housing or shell of the pump is rigid and does not deflect when the drug reservoir changes in size.

Figure 2A:
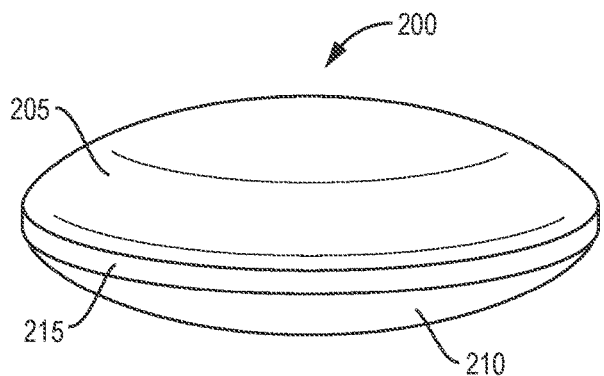
FIG. 2A is a perspective view of a filled drug chamber in accordance with embodiments of the invention.
Figure 2B:
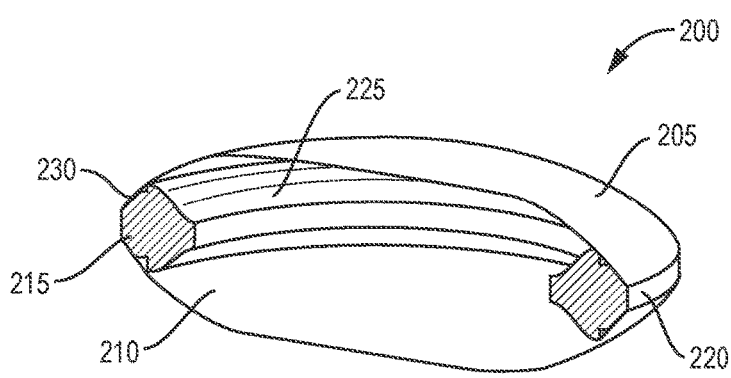
FIG. 2B is a cutaway view of the drug chamber shown in FIG. 2A.
Figure 2C:
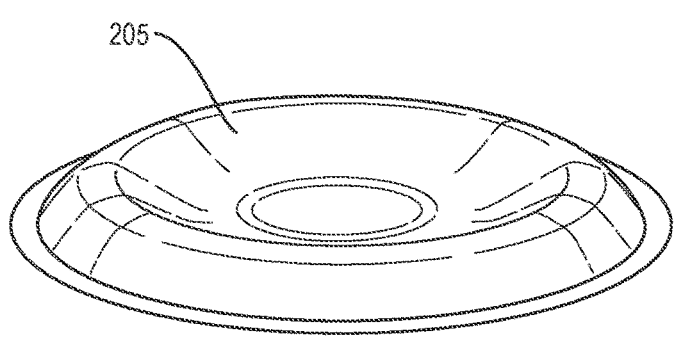
FIG. 2C is a perspective view showing, in a collapsed configuration, one of the membranes defining the drug chamber.

In one embodiment, illustrated in FIGS. 2A-2C, the drug reservoir 200 has two flexible, opposed hemispheric membranes 205, 210 attached to opposite sides of a ring-shaped equatorial rib 215. The membranes 205, 210 may be metalized or comprise two or more layers of different material to provide a more reliable and permanent barrier than a simple single material diaphragm. The equatorial rib 215 may have a flat outermost surface 220 and oppositely beveled interior surfaces (indicated, on the top side, at 225, 230, with identical surfaces on the bottom side of the rib 215) that extend from rounded top and bottom ridges. As the hemispheric membranes 205, 210 collapse with the dispensing of liquid from the drug reservoir 200, they are supported by the beveled interior surfaces 225, 230 so as to avoid regions of material stress. Similarly, the upper and lower ridges of the rib 215 are rounded to avoid stress concentrations along the annular regions of contact. This design allows for maximum exposure of the surface interfaces of the flexible membranes 205, 210 with the propellant chamber (or the propellant directly). The membranes 205, 210 may be joined to the rib 215 by thermal or ultrasonic welding or by adhesion using, for example, a medical-grade epoxy. The membranes 205, 210 may be manufactured from, for example, a biocompatible material such as silicone or parylene-C. The rib 215 may be a rigid biocompatible material (e.g., metal or a polymer such as medical-grade polypropylene, PEEK).

One or more bores may extend through the rib 215 from its exterior surface 220 to facilitate dosing and refilling of the drug chamber 200. In some embodiments, the bores are diametrically opposed so that the inflow and outflow vectors are parallel, thereby reducing flow turbidity and shear stresses to the membranes 205, 210 and attachment points when the interior is flushed. These effects are enhanced by the deflection vectors of the flexible membranes being perpendicular to the drug flow vectors.

In some embodiments, there is only one flexible membrane to allow a bellows (in the case of a corrugated membrane) or dome (in the case of a smooth membrane) expansion to occur during the actuation and refill processes. In this embodiment, useful for treatment of the eye, the shell of the pump (described below) is curved to fit the outer radial curvature of the eye and can be implanted under the conjunctiva similar to the placement of a glaucoma drainage device. In other embodiment, the membranes 205, 210 are a single, continuous piece of material that encapsulates the equatorial rib 215.

Figure 2D:
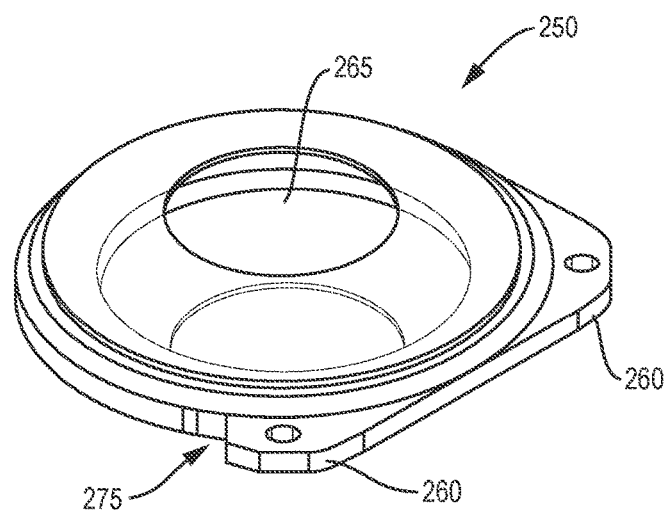
FIG. 2D is a perspective view of a carrier frame for the drug chamber.
Figure 2E:
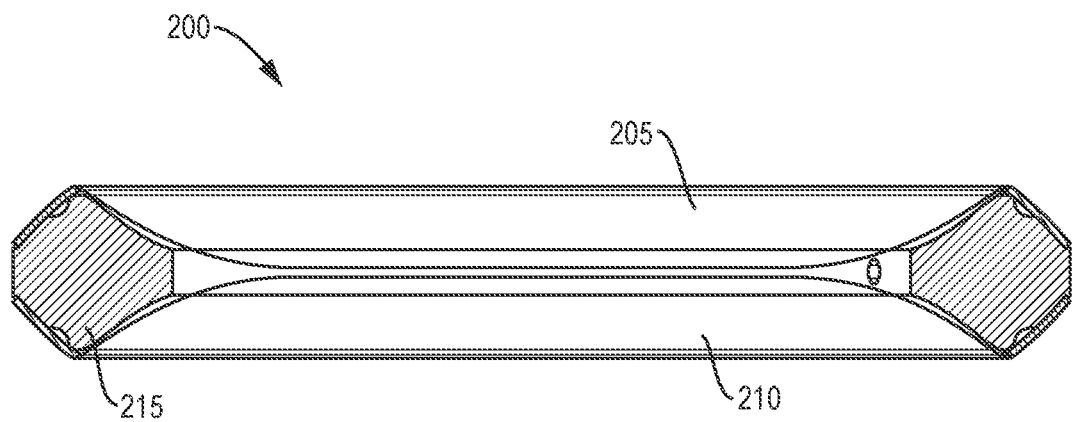
FIG. 2E is a sectional view showing the drug chamber in a collapsed configuration, as in FIG. 2C.

FIG. 2E shows the drug reservoir 200 in a nearly depleted configuration. The curvatures on the internal circumference of the equatorial rib 215 allows the actuation membranes 205, 210 to collapse evenly and maintain a small gap therebetween, preventing the two membranes from sticking together. Unlike other drug pump systems that rely on an elastic membrane (e.g., a balloon) to inflate and contract during pumping cycles, the drug reservoir 200 merely changes its deflection profile with minimal if any contraction or stretching of the membrane material. Because contraction and inflation require surrounding headroom, this mode of operation precludes space-efficient designs that minimize empty volume. The membranes 205, 210 may be flexible yet not very elastic. Because they do not undergo repeated cycles of stretching and relaxation, the membranes 205, 210 may be more durable. If the membranes are designed to touch, they may be coated with an inert material that does not interact with the drug, but also minimize stiction forces so that they may easily separate when the drug reservoir is refilled. Exemplary inert coatings may include silicone dioxide, which is used to coat the inside of drug vials to minimize protein absorption of biologics. Alternatively, parts of the surfaces are textured or roughened during manufacture to reduce the contacting surface area.

Additionally, the above approach promotes minimal drug reservoir volume upon depletion, which allows for better drug flushability and refillability to efficiently remove any debris, drug aggregate, and air bubbles. For example, in the case of 80% refillability, where only 80% of the total drug volume in the reservoir can be removed, the refilled drug reservoir would consist of a mixture of 20% old drug and 80% new drug. Even if the drug reservoir is refilled two or three times, the mixture will consist of 4% or 0.08% old drug, respectively. Comparatively, in a drug reservoir design with 95% refillability, where 95% of the total drug volume in a reservoir can be removed, the refilled drug reservoir would consist of a mixture of 5% old drug and 95% new drug. If the drug reservoir is refilled two or three times, the mixture would consist of 0.25% and 0.01% old drug, respectively, thereby efficiently removing almost all old drug.

The drug reservoir may be held within a frame 250 as shown in FIG. 2D. The frame 250 includes a pair of alignment and retention tabs 260 and defines an interior region having a circular interior edge 265. Top and bottom dome members 270 have central circular openings. In use, the drug reservoir 200 is introduced into the frame 250 with the outer edge 220 of the rib 215 sized to fit securely against the interior frame edge 265. One or more ports 275 extend through the frame 250 and align with the bore(s) through the rib 215 of the drug reservoir 200, thereby facilitating fluid communication with the interior of the drug reservoir 200 for filling and flushing operations (and, in some embodiments, providing redundant flow paths in case one or more of the paths become clogged with, e.g., debris or aggregate). In some embodiments, the top and bottom membranes 205, 210 of the drug reservoir 200 have circular flat surfaces 270. When the reservoir and frame are mounted within a propellant chamber as described below, the circular openings of the dome members 270 allow the surrounding propellant to act on the top and bottom membranes 205, 210.

Figure 2F:
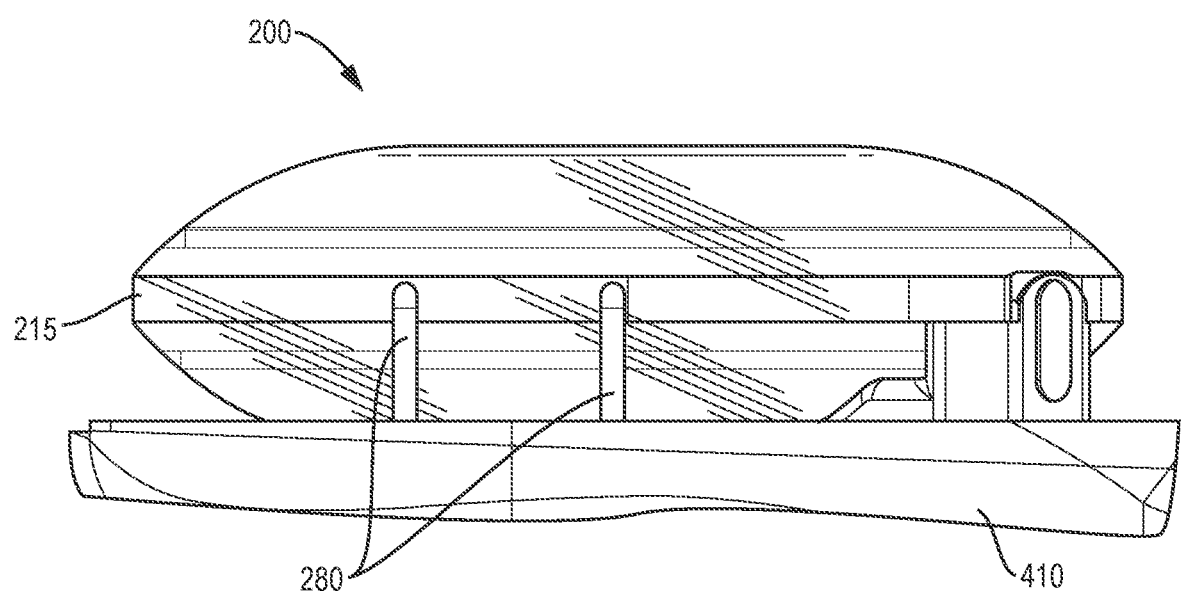
FIG. 2F is an elevation showing fluidic connections between the drug chamber and an external refill port.

Fluidic connections between the drug chamber 200 and the exterior of the pump are shown in FIG. 2F. One or more conduits 280 are inserted into bores through the equatorial rib 215 and lead to a refill port in the housing through the ante-chamber, as described below.

The flow restrictor 130 enables the pump 100 to operate and be refilled without valving. The flow restrictor 130 may, for example, permit flows on the order of 1 μL per day. Such a low flow rate enables the drug reservoir 105 to be refilled without a large surge in delivery rate. The pump can be "always on" with the outgoing flow rate matched to a target drug-infusion rate. The low flow rate also permits the pump 100 to be packaged for shipment with the drug reservoir 105 filled with water. When the pump is implanted for use, the water remaining in the drug reservoir 105 can be purged and replaced with drug, which will gradually replace the remaining water in the flow restrictor 130 as the water exits the cannula 122 at the pump's inherent discharge rate.

As shown in FIG. 3A-3D, the flow restrictor may take the form of a microfluidic chip 300, which maximizes the flow resistance control in a minimal space. The flow-restrictor chip 300 includes a top layer 310 and a bottom layer 320 joined into a single chip structure. The inlet port 335 to the chip 300 is in the center of a circular region of the top layer 310 with radially arranged raised supports 340; these prevent warping or collapse of the overlying filter membrane 125a through which drug filters, funnel drug into the inlet port 335, and may act as a flow-restrictor inlet filter. The outlet port 345 fluidically communicates with the flow path to the cannula 122.

To establish the flow resistance, a microfluidic restriction flow path 355 is etched on the bottom layer 320, in a space-efficient pattern (e.g., a radially reducing spiral as illustrated, a zig-zag path, a rectangular reducing spiral, serpentine path, etc.). The pattern is selected to create the desired flow resistance within the dimensions of the bottom layer 320. In alternative embodiments, the microfluidic restriction flow path is etched on the top layer 310, or on both the top layer 310 and bottom layer 320. The flow path distances between one or more inlets one or more outlets and the cross-sectional dimensions of the flow-restriction pathways control the overall volumetric flow rate Q of the drug at the outlet according to the Hagen-Poiseuille law, $$Q = \frac{\pi \Delta P R^4}{8 \eta L}$$

where ΔP is the pressure difference, R is the radius of the flow path, η is the dynamic viscosity, and L is the length of the flow path. In embodiments where the cross section is not circular, the relationship is modified to accommodate other shapes (oval, rectangular, etc.). In one example, the flow-path channel has a cross-sectional area of 75 µm² (e.g., 5 µm×15 µm cross-section). In another example, the channel has a cross-sectional area of 100 µm² (e.g., 10 µm×10 µm cross-section). In yet another example, the channels are 10 µm×20 µm cross sections creating a cross section of 200 µm². In yet another example, the flow-path channel is 20 µm×20 µm for a cross-sectional area of 400 µm² In many embodiments, this range of cross sections enables a drug delivery device to deliver ultra-low flow rates between 0.1 µL/day to 20 µL/day. The flow rate also depends on the viscosity of the drug; whereas water has a viscosity of 1 centipoise at 20° C., a drug with a higher viscosity of 1.5 centipoise would have a lower flow rate. The viscosity of the drug also changes with temperature.

Figure 3A:
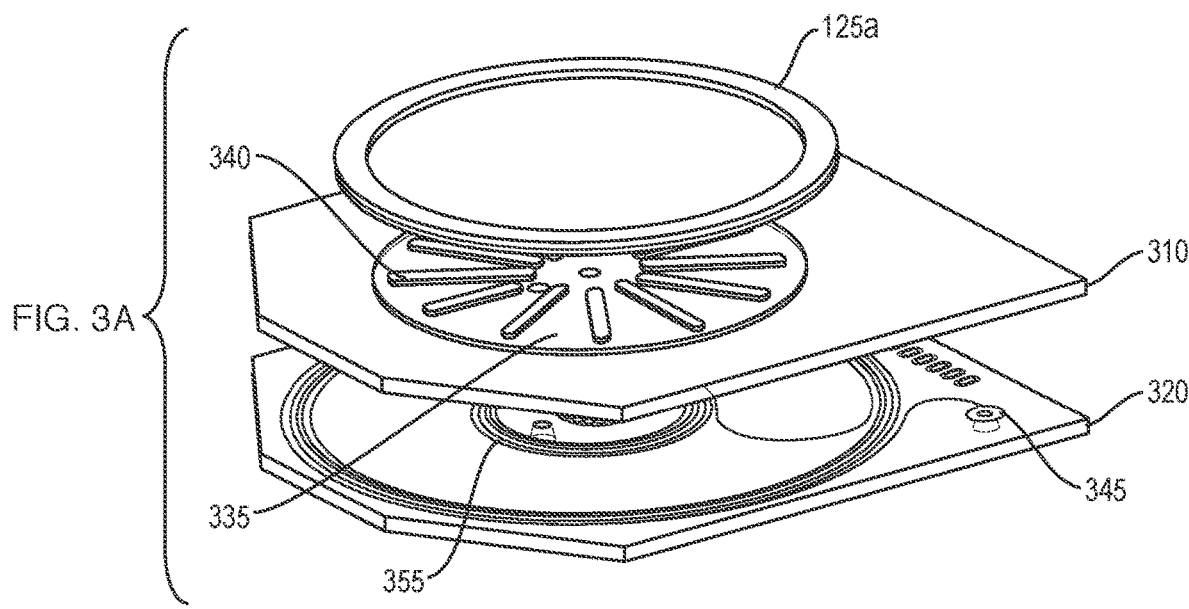
FIG. 3A is an exploded view of a flow restrictor chip in accordance with embodiments of the invention.
Figure 3B:
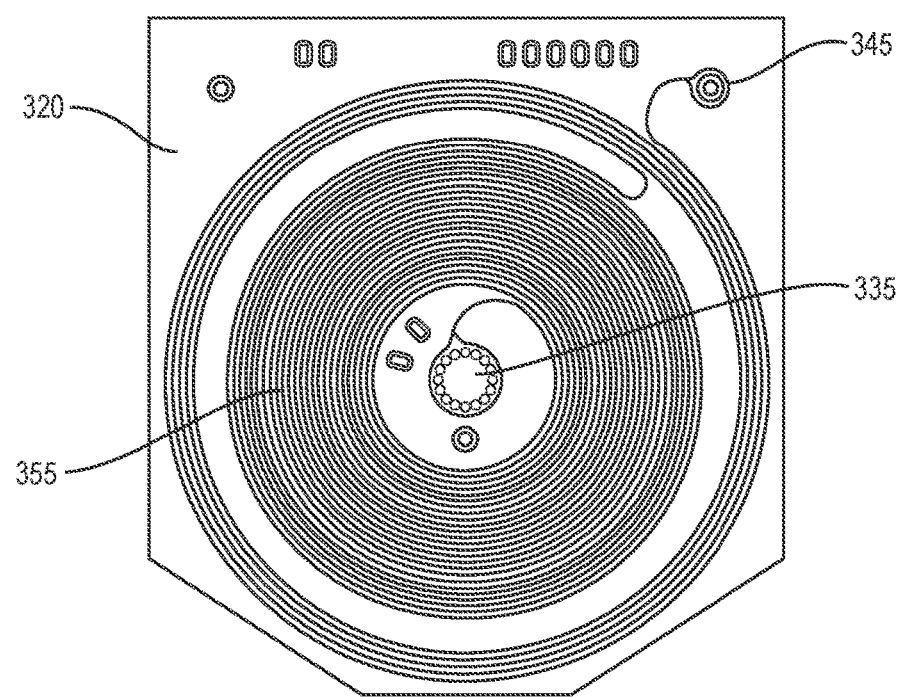
FIGS. 3B and 3C are plan views of microfluidic layers of the flow-restrictor chip with different flow-path lengths.
Figure 3C:
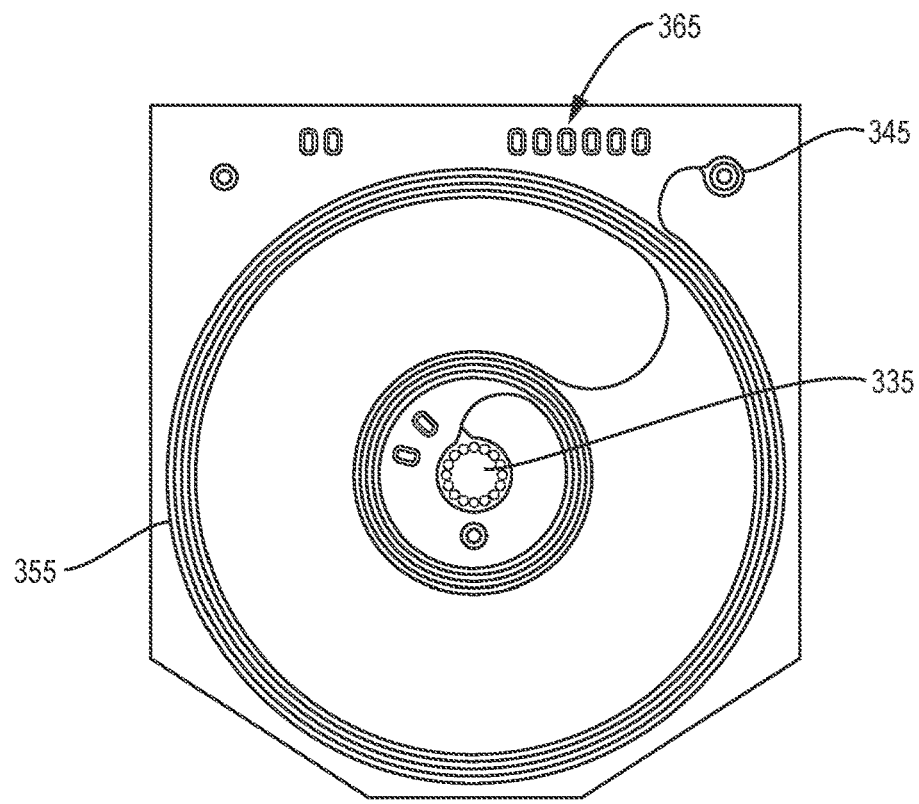
Figure 3D:
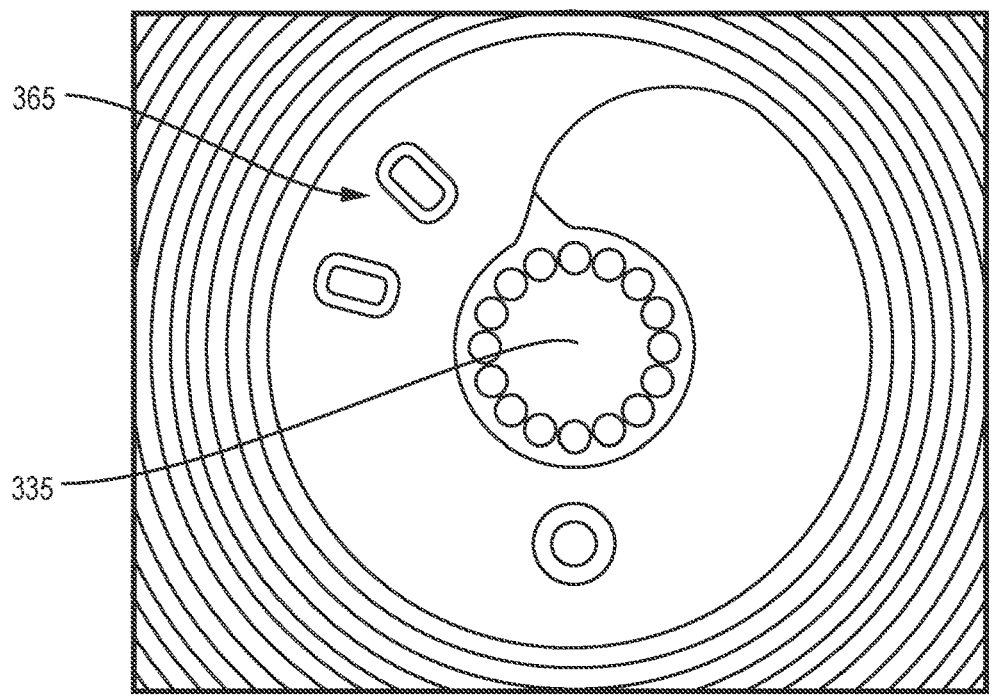
FIG. 3D is a detailed plan view of the inlet portion of the microfluidic layer top surface shown in FIG. 3A.
Figure 3E:
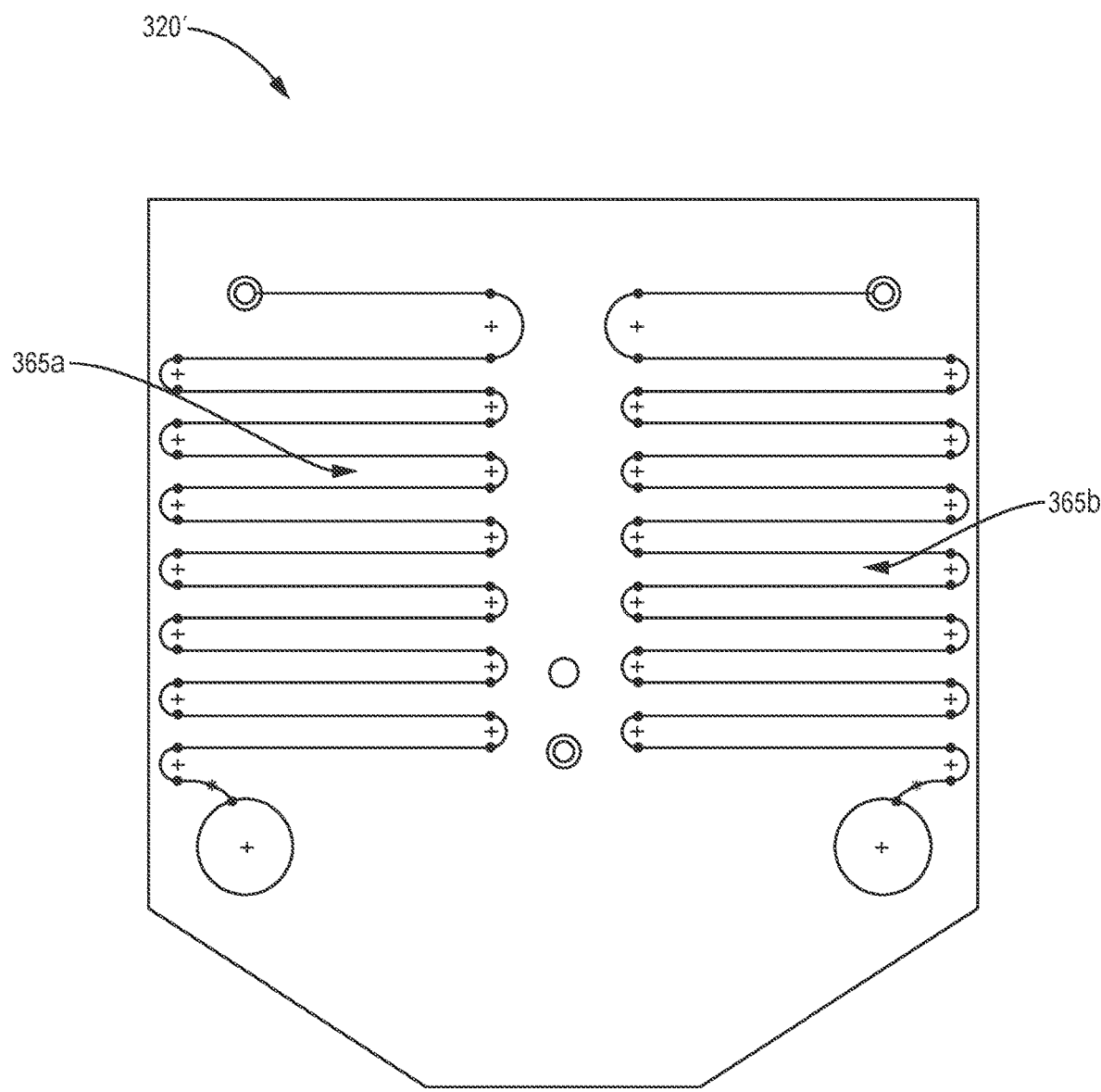
FIG. 3E is a plan view of a flow-restrictor chip having two independent flow paths.

The flow-restrictor chip 300 is conventional; pattern selection and etching procedures to achieve a desired flow resistance within given layer dimensions are readily achieved without undue experimentation by those skilled in the art. FIGS. 3B and 3C illustrate embodiments using the same chip footprint with different flow-path lengths. If a target flow resistance cannot be achieved in a single bottom layer 320, multiple such layers may be stacked and fluidically connected to extend the effective length of the flow path. Similarly, FIG. 3E shows a bottom layer embodiment 320' having two flow paths 365a, 365b; this embodiment is useful when the drug-delivery device is designed to deliver two different drugs independently from two drug reservoirs via two cannulas.

In certain embodiments, the bottom layer 320 may include a ring of pillars, as illustrated, to provide additional support and prevent warping or collapse near the inlet—is in fluid communication with the entry to the flow path 355. The ring of pillars may additionally function as a filter. The outlet port 345 expels liquid at the delivery rate enforced by the flow path. Both the top layer 310 and the bottom layer 320 include through-holes 360 which, when aligned, provide a fluid path through the layers 310, 320. In this embodiment, this fluid path ultimately leads from the refill port 135 to the drug reservoir 105 via the ante-chamber 140 (see FIG. 1B). In certain embodiments, each layer 310, 320 has one or more orientation-specific characters 365, e.g., part number, serial number, or other identifying characters that help distinguish the top and bottom surfaces thereof.

FIGS. 4A-4E illustrate how the components described above can be combined and assembled into an implantable drug pump, e.g., for ocular applications. A base 405 includes a bottom housing portion 410 including an extension 412 that terminates in a cannula 415. In certain embodiments, the cannula 415 is made of a transparent or translucent material, allowing the drug flow to be visible.

Figure 4B:
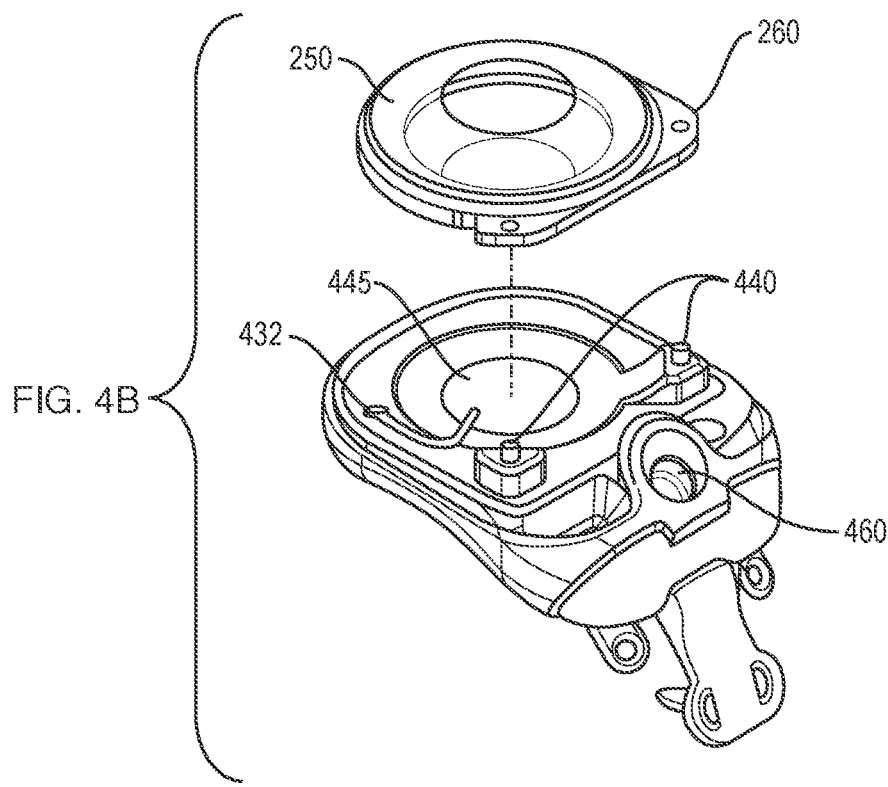
FIG. 4B is an exploded view showing placement of the drug chamber and its carrier frame in the lower housing member.
Figure 4C:
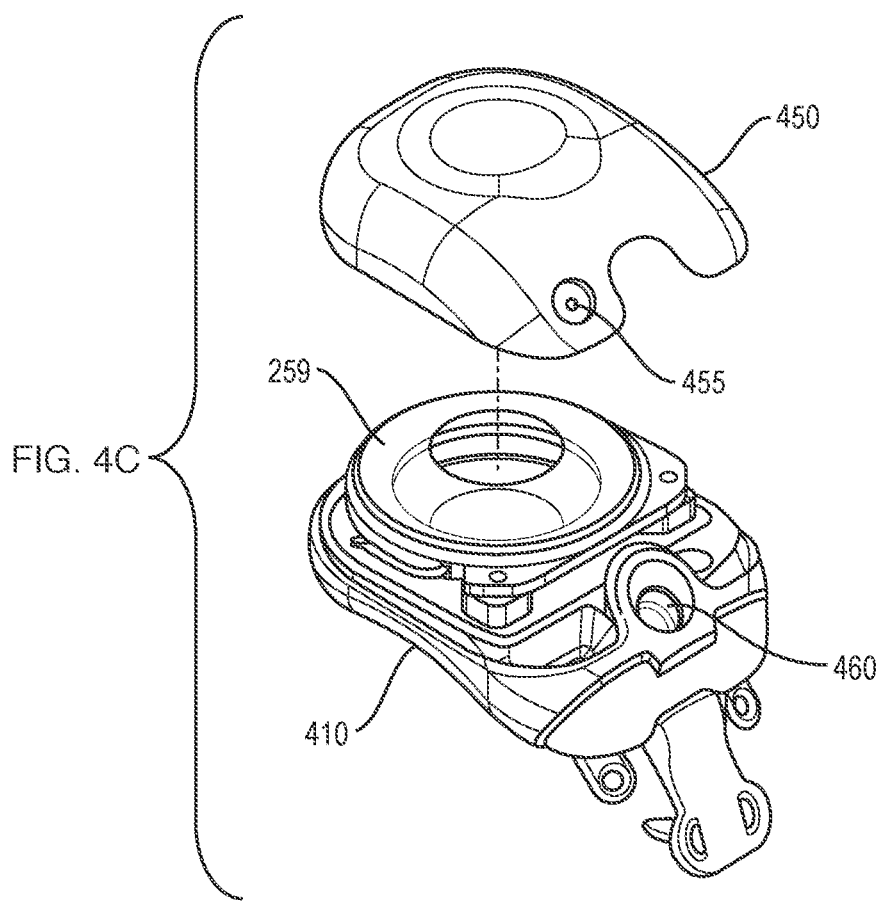
FIG. 4C is an exploded view showing placement of an upper housing member over the lower housing member and the drug chamber seated therewithin.
Figure 4D:
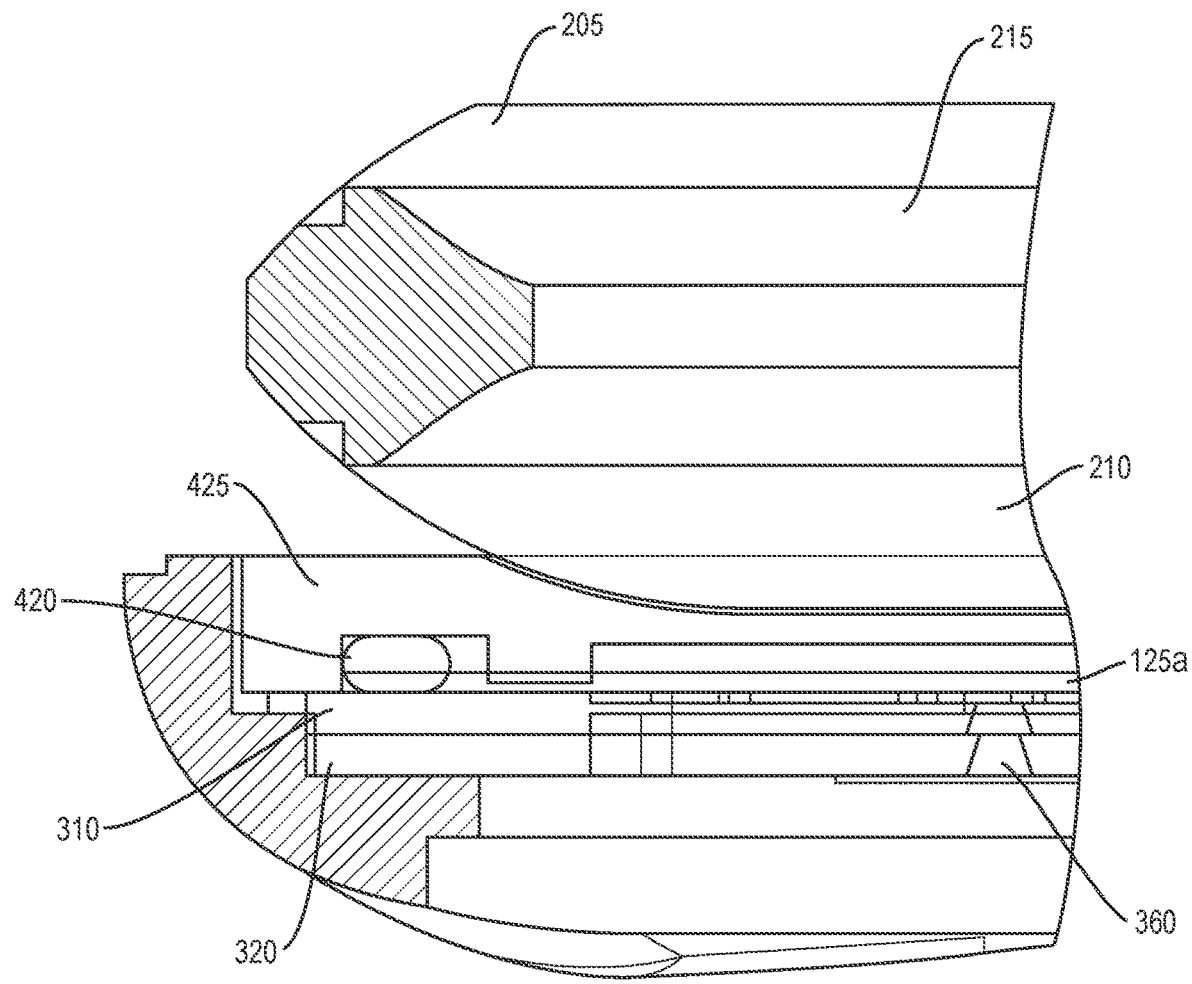
FIG. 4D is a partial cutaway elevation of a portion of the drug reservoir seated within the lower housing member.

The bottom contour of the housing portion 410 and the extension 412, as well as angle formed between the cannula 415 and the extension 412, are designed to conform to the anatomy of implantation as described below. The flow-restrictor chip 300 seats on the recessed floor 418 of the housing portion 410. The refill through-hole 360 and outlet port 350 overlie and communicate with fluid lines through the floor 418; a pair of sealing gaskets or o-rings 420 prevent leakage. The fluid line from the outlet 350 leads through the cannula 415, and the line from the refill through-hole 360 is in fluid communication with the refill port 460 (see FIG. 4E). The bacterial filter 125a overlies the inlet to the flow-restrictor chip 300. A support 425 for the drug chamber seats stacks above the flow-restrictor chip 300 and the bacterial filter 125a, and leakage with respect to the inlet to the chip 300 and the through-hole 360 is prevented by respective sealing gaskets or o-rings 427, 430. The ante-chamber 140 is formed between the flow restrictor chip 300 and the support 425. A conduit 432 fluidly connects the drug chamber (through the rib 215), which seats against a contoured edge 435 of the support 425, to the underlying ante-chamber. In this embodiment, the support 425 further has a step on the bottom surface interfacing the flow-restrictor chip 300 to add additional height to the ante-chamber 140. Additional gaskets may be added to ensure that fluid-tight seals are made between the components. The partially assembled pump, with the support 425 seated within the housing portion 410, is shown in FIG. 4D.

The frame 250 for the drug reservoir (not shown) is mounted to the support 425 so that apertures through the alignment tabs 260 receive complementary alignment posts 440. The bottom open portion of the frame 250 overlies the opening 445 through the bottom of the support 425 and exposes a portion of the lower membrane 210 (see FIGS. 2A and 2B) of the drug reservoir 200. With reference to FIG. 4C, an upper housing portion 450 is welded or otherwise sealingly affixed to the bottom housing portion 410, thereby creating the propellant chamber therewithin (as explained in greater detail below). The upper housing portion 450 includes an needle entry port 455 for introduction of propellant into the propellant chamber. The entry port 455 may be an elastomeric septum, but in some other embodiments may be welded shut (e.g., filled with a weld cap) following introduction of propellant. A refill entry port 460 may likewise contain a self-sealing elastomeric septum to facilitate repeated refills via a needle. The refill port 460 communicates fluidically with one of the bores 220 through the equatorial rib 215 (see FIG. 2B). Examples of suitable self-sealing materials for needle-entry ports include, but are not limited to, nylons, cellulose, gelatin, silicone rubbers, porous rubbers, and other elastomeric materials.

The cannula 415 may be a tube made of titanium or silicone, or may be a clear tube made of a PEEK, polyimide or polyamide, or any suitable biocompatible and drug-compatible material. In one embodiment, the cannula is overmolded with silicone, thereby making a shroud, which is more flexible and durable. In embodiments, the refill port 460 is also made of a transparent or translucent material, and the shroud may extend through the bottom housing portion 410 toward the refill port 460, allowing light to illuminate the refill port from underneath. In alternative embodiments, additional surrounding areas of the refill port (e.g., the bottom, or a portion of the side wall curvature) may be transparent. Such functionality may be used during refill by a surgeon by using an endo-illuminator to focus light through the cannula; the light scatters through the translucent cannula material to illuminate the refill port for easy location.

Figure 4E:
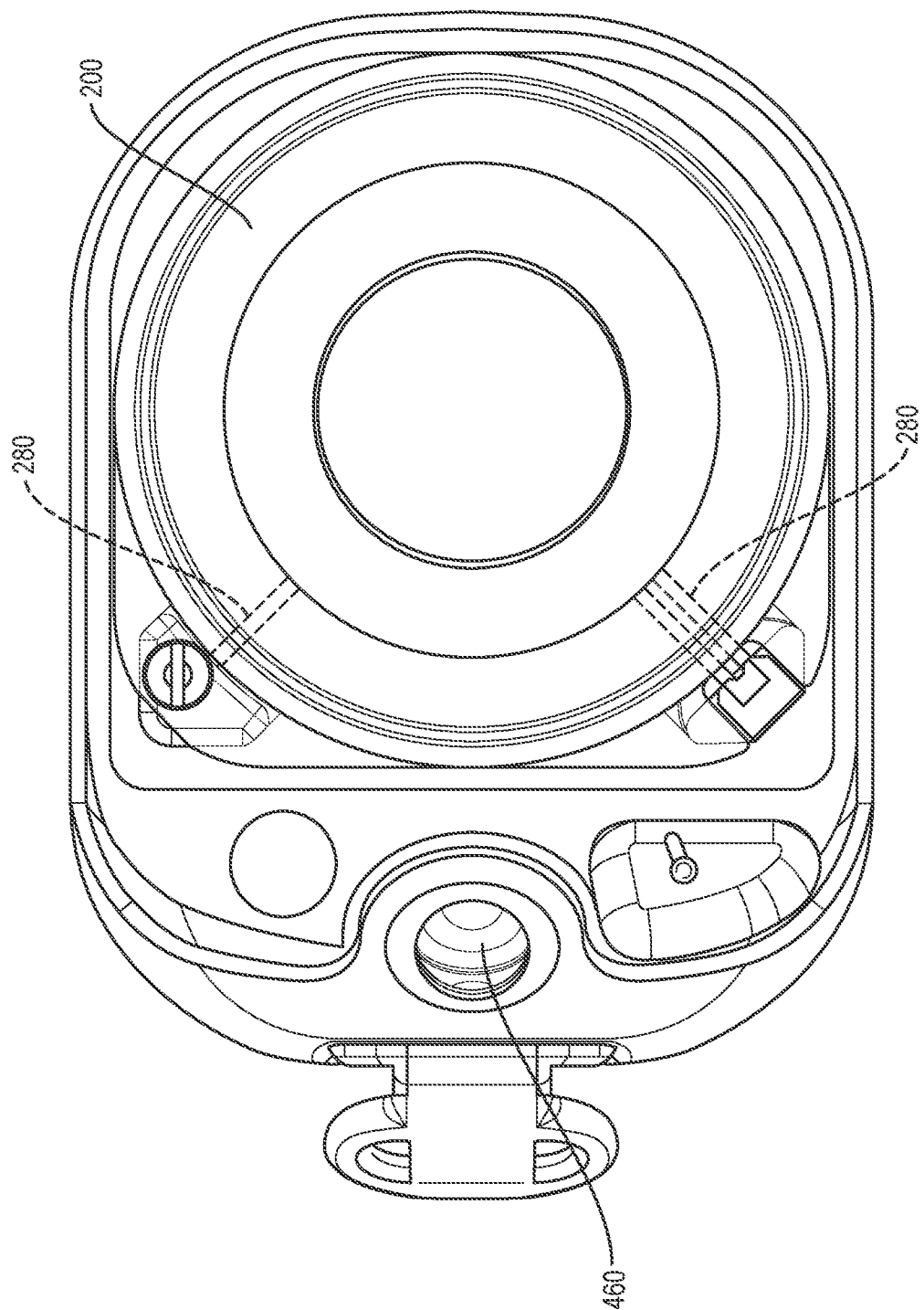
FIG. 4E is a plan view of the assembled drug pump.
Figure 5A:
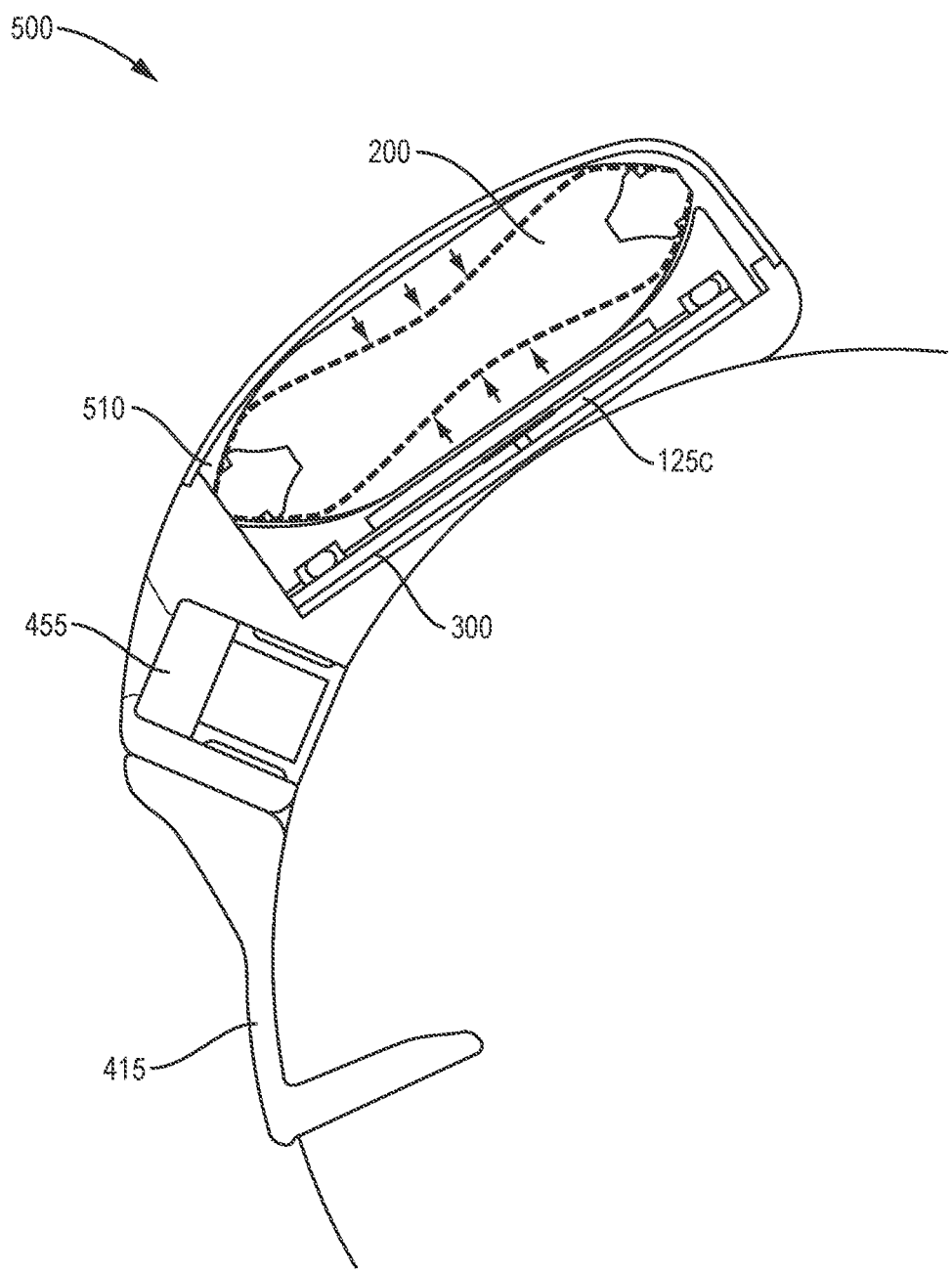
FIG. 5A is a sectional elevation showing an embodiment of the invention positioned for use along an anatomical contour.
Figure 5B:
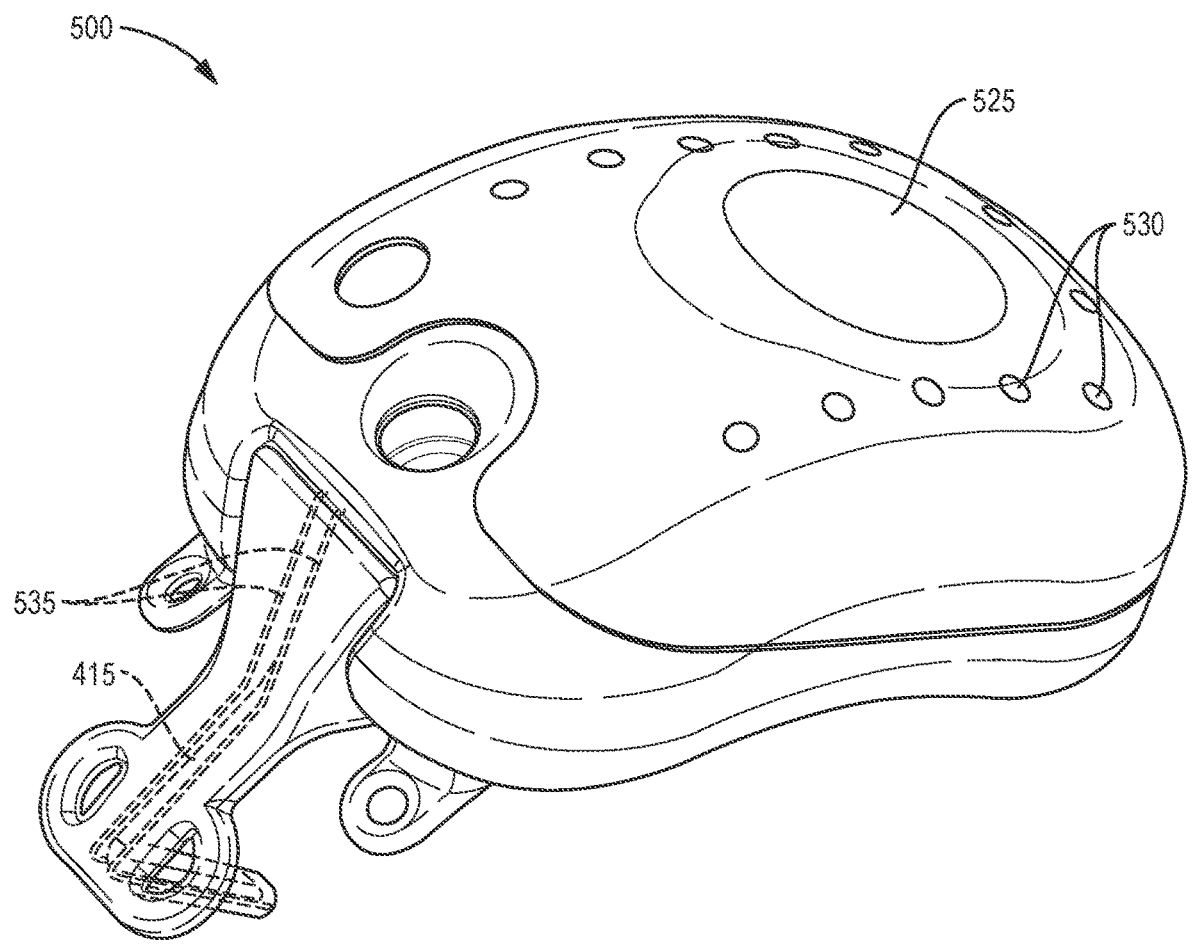
FIG. 5B is a perspective view of an embodiment of the invention configured for ocular applications including glaucoma drainage.

The assembled unit 500 is shown in FIGS. 4E, 5A and 5B. FIG. 4E, in particular, illustrates an embodiment with multiple flow conduits 280 that fluidically couple the drug reservoir 200 to the refill port 460. Single conduits or sets of conduits may be offset from each other at a desired angle (e.g., 90°) to optimize fluid ingress and egress. With reference to FIG. 5A, the propellant chamber 510 is formed within the headspace of the upper housing portion 450. In the constant-pressure embodiment, the propellant chamber is filled with propellant(s) at a pressure sufficient to fully collapse the drug reservoir 200 when all drug is dispensed through the cannula 122. That is, the pressure exerted by the propellant remains sufficient to ensure that, even as the drug reservoir 200 empties, its contents will consistently exit the pump.

After implantation of the device 500, the drug may be modified with various drug vehicles of different viscosity to further vary the flow profile of the drug with each refill. Alternatively or in addition, the propellant chamber may have a separate refill port 455 through which a different propellant type, volume, or combination may be introduced to alter the flow profile. Certain propellants may further have adjustable pressures that are controlled through heating. Highly temperature-sensitive propellants still provide fairly constant drug flow when implanted, as the internal body temperature remains substantially constant most of the time. The device temperature may be manipulated by various methods including inductive heating, embedded electric heaters powered through a telemetry system, and ultrasound two-part material agitation, to name a few.

In some applications, it may be desirable to permit a physician to stop or alter the prescribed treatment at any time. This may be accomplished, for example, using a nitinol valve that may be reversibly or irreversibly actuated from a primary position to a secondary position by refilling (and optionally removing from) the drug reservoir a fluid having a temperature beyond the normal range experienced by the location (the normal range being, e.g., 30° C. to 40° C.). The nitinol valve, which may be located in the refill port or in a fluid-path conduit, may have a latching position activated when the contents of the drug reservoir are above the normal temperature range, thereby maintaining the open or closed position of the fluid path.

Alternatively, a valve may be responsive to a magnetic field. For example, the valve may exhibit a deliberately weak response so that a strong, highly focused high magnetic field is necessary for actuating the valve. In such embodiments, the magnetic field may be produced by a handheld device or wand.

In many embodiments, the device 500 does not require any electronics. However, various embodiments can incorporate electronics for monitoring device functionality, the device 500 may contain internal sensors to meter the amount of drug dispensed or remaining within the drug reservoir. Metering may be achieved by monitoring the fill level of the drug reservoir or through use of a fluid sensor, e.g., a time-of-flight sensor, to continuously monitor flow and thereby derive the volume delivered. In other embodiments, the device contains few or no internal sensors so that more of the internal device volume can be used by the drug reservoir. In this case, the drug reservoir volume and drug volume delivered over time can only be assessed during the refill process. The refill system may contain a metering system to record the amount of fluid injected and/or evacuated from the drug reservoir as well as a pressure sensor to evaluate when the reservoir is full or empty.

The illustrated device 500 is shaped for placement on, e.g., the sclera under the conjunctiva of the eye and the cannula 415 is inserted through to the posterior chamber of the eye. The device 500 administers fluid to the posterior segment through the cannula 415. In other embodiments, the device 500 can administer fluid to the anterior chamber of the eye, which is separated from the posterior chamber by the lens. In still other embodiments, the device 500 is implanted in other portions of the body that may benefit from therapeutic fluid delivery (e.g., in the sub-arachnoid space of the brain for providing chemotherapy or in the pancreas).

Features that make the device 500 particularly suited to ocular applications are illustrated in FIG. 5B. A shell plate 525 with drainage holes representatively indicated at 530 is placed above the original shell 450. In this embodiment, intraocular pressure (TOP) drainage cannulas 535 extend from the shell plate 525 and are positioned parallel to the drug-delivery cannula 415 within the same silicone overmold. This embodiment is useful when simultaneous anterior chamber fluid drainage and anterior chamber drug delivery is required. To ensure adequate drug delivery instead of a large portion of drug delivered being drained, the drug-delivery cannula 415 preferably extends further into the anterior chamber, whereas the TOP drainage cannulas 535 terminate closer to the interior surface of the anterior chamber.

In some embodiments, a drug pump in accordance herewith may additionally contain one or more check valves with a zero or near zero cracking pressure, and which close sufficiently to stop any flow when there is no forward flow pressure or in response to a net reverse pressure. Such valves may be strategically placed through the cannula 415 and/or after the flow restrictor 300. Although the propellant chamber 110 provides constant forward pressure through the cannula 122, in case such forward pressure ceases (e.g., drug reservoir is empty, increase of target site pressure over that of the propellant pressure), no backward flow would occur into the cannula.

Figure 1C:
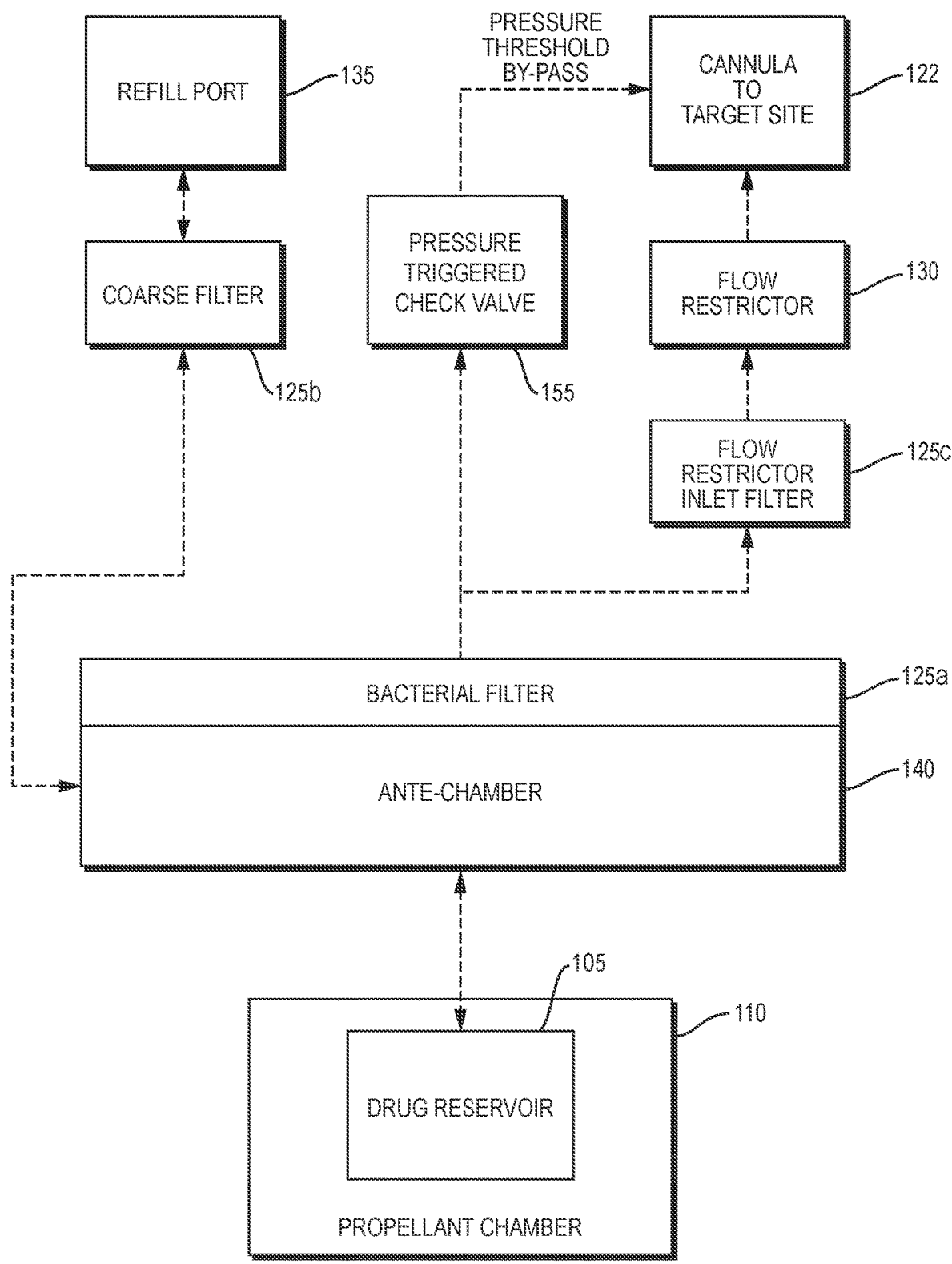
FIG. 1C schematically illustrates components of an alternative embodiment.

In an alternative embodiment, shown in FIG. 1C, the drug pump device 100' has a pressure-threshold bypass fluidic path that conveys fluid injected from the refill port 135 to the cannula 122. The pressure-threshold bypass fluidic path includes a one-way pressure-triggered check valve 155, which opens only when a certain pressure threshold is passed. This threshold may exceed the propellant chamber pressure by a fixed amount. For example, the intraocular pressure is normally 15 mm Hg or 0.29 psi. In one embodiment, if the desired internal pump pressure is 7 psig at body temperature, the propellant chamber is filled to a pressure of 7 psig, which is higher than the intraocular pressure; consequently, the propellant pressure will be sufficient to push drug through the flow restrictor 130 and out of the cannula 122 into the target site. A normal refill will require a pressure greater than 7 psig (e.g., 11 psig) to overcome the pressure of the propellant chamber 110 and thereby fill the drug reservoir 105. The pressure-triggered check valve 155 may have a cracking pressure of 15 psig which, when reached, would allow drug to flow directly through the cannula 122 to the target site, bypassing the flow restrictor 130.

The use of the pressure-threshold bypass fluidic path may be useful in various contexts. In one usage, an extra dose of a specified amount may be injected directly to the target site at the time of refill. The refill amount equals the sum of the drug-reservoir fill volume and the extra dose volume (e.g., 200 µL+20 µL=220 µL).

In another embodiment, if the pump malfunctions (e.g., no flow through the flow restrictor, propellant chamber pressure loss, deliberate halt to the pump's function by removing propellant, etc.), the bypass fluidic path can be used as a path for a standard intravitreal injection (IVT injection). This affords an easily located drug-refill port, which can be accessed through the conjunctiva without measuring for accurate positioning of an IVT injection. In addition, as the cannula 122 has permanent access to the target site, no new access into the vitreous is required, obviating the possibility of certain adverse events such as vitreoretinal traction, retinal tears, and retinal detachment. Also, the IVT needle-insertion depth into the refill port is limited by the device structure, so adverse events (e.g., tissue damage) stemming from excess needle insertion are avoided. Finally, due to the flow path configuration, the drug reservoir can be filled with one drug, and a second drug may be injected through the same refill port, which will force the second drug to be delivered immediately, whereas the first drug will be delivered slowly over a set period of time thereafter.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An implantable pump comprising:
   a rigid housing;
   within the rigid housing, a drug reservoir having a first expandable membrane and a second expandable membrane affixed to an equatorial rib, the first and second expandable membranes defining a drug chamber between the first and second expandable membranes for containing a liquid medicament, the equatorial rib including a portion extending radially inward between the first and second expandable membranes and having beveled interior surfaces, the equatorial rib and the first and second expandable membranes being configured such that the first and second expandable membranes contact the beveled interior surfaces when the drug chamber is depleted, or being depleted, of the liquid medicament, but do not contact the beveled interior surfaces when the drug chamber is filled with the liquid medicament;
   a propellant chamber occupying an interior space of the rigid housing, the propellant chamber containing the drug reservoir and a propellant therein, the propellant exerting a substantially constant pressure on the drug reservoir;
   a cannula in fluid communication with the drug reservoir; and
   a flow restrictor between the drug reservoir and the cannula.

2. The implantable pump of claim 1, wherein the first and second expandable membranes are affixed to first and second opposed sides of the equatorial rib, the first and second opposed sides of the equatorial rib having rounded ridge profiles to limit material stress on the first and second expandable membranes when in contact therewith.

3. The implantable pump of claim 1, further comprising a refill port fluidically coupled to the drug reservoir and having a self-sealing entry port in the rigid housing.

4. The implantable pump of claim 3, further comprising a pressure-threshold bypass fluidic path for conveying to the cannula fluid injected through the refill port.

5. The implantable pump of claim 4, further comprising a pressure-triggered check valve in the bypass fluidic path.

6. The implantable pump of claim 1, wherein the flow restrictor is sized to permit an outflow from the cannula ranging from 0.1 µL/day to 20 µL/day.

7. The implantable pump of claim 1, wherein the flow restrictor has a fluid path with a cross-sectional area ranging from 50 µm$^2$ to 400 µm$^2$.

8. The implantable pump of claim 1, wherein the flow restrictor is a microfluidic chip.

9. The implantable pump of claim 1, further comprising:
   a filter and an ante-chamber, the ante-chamber intervening between the drug reservoir and fluid lines leading to the cannula and a refill port in the rigid housing for filling the drug chamber, the ante-chamber facilitating flushing of the filter through one of the fluid lines.

10. The implantable pump of claim 9, wherein the first and second expandable membranes are affixed to first and second opposed sides of the equatorial rib, the first and second opposed sides of the equatorial rib having rounded ridge profiles to limit material stress on the first and second expandable membranes when in contact therewith.

11. The implantable pump of claim 1, wherein the propellant has a pressure sufficient to eject all liquid contents of the drug reservoir.

12. The implantable pump of claim 1, wherein the propellant is a material mixture that generates a total pressure greater than a pressure at a target site at body temperature.

13. The implantable pump of claim 1, wherein the equatorial rib has at least one bore therethrough.

14. The implantable pump of claim 13, wherein the at least one bore comprises at least two diametrically opposed bores.

15. The implantable pump of claim 13, wherein the at least one bore extends in a direction perpendicular to a direction of compression of the drug reservoir by the propellant.

16. The implantable pump of claim 1, further comprising:
   an ante-chamber between the drug reservoir and the flow restrictor.

17. The implantable pump of claim 16, further comprising at least one filter in line between the drug reservoir and the flow restrictor.

18. The implantable pump of claim 16, wherein the first and second expandable membranes are affixed to first and second opposed sides of the equatorial rib, the first and second opposed sides of the equatorial rib having rounded ridge profiles to limit material stress on the first and second expandable membranes when in contact therewith.

19. The implantable pump of claim 1, further comprising at least one filter in line between the drug reservoir and the flow restrictor.

20. The implantable pump of claim 1, further comprising a propellant fill port including a self-sealing elastomeric septum.

21. The implantable pump of claim 1, wherein the propellant has a pressure adjustable by heating.

22. The implantable pump of claim 1, further comprising at least one drainage cannula.

23. The implantable pump of claim 1, wherein the implantable pump includes no internal circuitry.

* * * * *